United States Patent [19]
Dodge et al.

[11] Patent Number: 6,054,278
[45] Date of Patent: Apr. 25, 2000

[54] RIBOSOMAL RNA GENE POLYMORPHISM BASED MICROORGANISM IDENTIFICATION

[75] Inventors: Deborah E. Dodge, Albany, Calif.; Douglas H. Smith, Centerville, Del.

[73] Assignee: The Perkin-Elmer Corporation, Foster City, Calif.

[21] Appl. No.: 09/073,465

[22] Filed: May 5, 1998

Related U.S. Application Data

[60] Provisional application No. 60/045,603, May 5, 1997.
[51] Int. Cl.[7] .............................. C12Q 1/68; C12N 25/11
[52] U.S. Cl. ........................... 435/6; 536/23.1; 536/24.33
[58] Field of Search ................................ 435/6; 536/23.1, 536/24.33

[56] References Cited

PUBLICATIONS

Innis et al. DNA sequencing with *Thermus aquaticus* DNA polymerase and direct sequencing of polymerase chain reaction–amplified DNA. Proc. Natl. Acad. Sci. USA vol. 85, pp. 9436–9440, 1988.

Clayton et al. Intraspecific variation in small–subunit rRNA sequences in GenBank: Why single sequences may not adequately represent prokaryotic taxa. Int. J. System. Bact. pp. 595–599, 1995.

Relman et al. The agent of bacillary angiomatosis. New Engl. J. Med. vol. 323 pp. 1573–1580, 1990.

*Primary Examiner*—John S. Brusca
*Attorney, Agent, or Firm*—Scott R. Bortner

[57] ABSTRACT

The invention relates the discovery that the polymorphisms in 16S rRNA genes may be used to identify unknown bacterial isolates at the level of species, subspecies and strain identification. The invention also relates to the discovery that the sequences of individual are required. The invention involves the generation of composite polynucleotide sequence of the 16S rRNA genes of a microorganism of interest. The invention is to provide methods for identifying microorganisms. The methods comprise the steps of generating a composite 16S rRNA region sequence from a microorganism of interest. The composite 16S rRNA region sequence reveals polymorphisms within the 16S ribosomal RNA gene of the microorganism. The composite 16S rRNA region sequence may then be compared with a list of previously obtained composite 16S rRNA region sequences from reference microorganisms so as to determine the species, subspecies, or strain of the microorganism of interest. Another aspect of the invention is to provide computer based methods of identifying a microorganism.

14 Claims, 1 Drawing Sheet

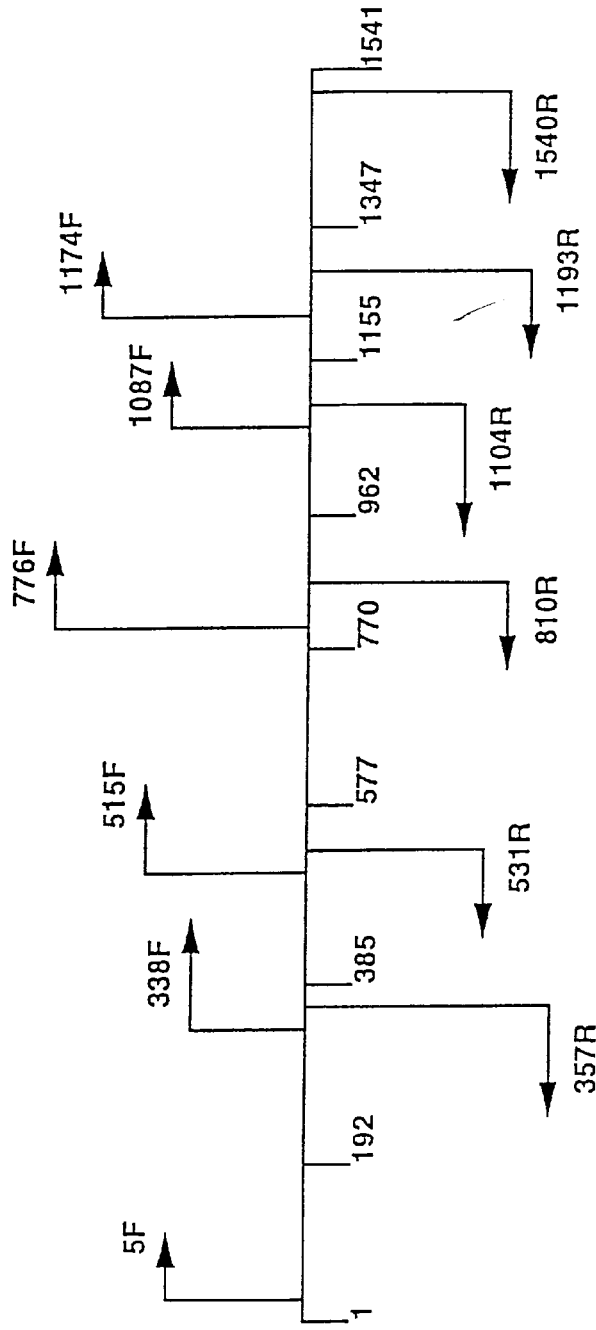
Fig. 1 16S rRNA Gene Map
* Primers are numbered from the 5' end of the primer on the forward strand of *E. coli* (J01859)

SEQUENCE LISTING

<160> NUMBER OF SEQ ID NOS: 17

<210> SEQ ID NO 1
<211> LENGTH: 23
<212> TYPE: DNA
<213> ORGANISM: Unknown Organism
<220> FEATURE:
<223> OTHER INFORMATION: Description of Unknown Organism: Bacterial

<400> SEQUENCE: 1
tggagagttt gatcctggct cag                                            23

<210> SEQ ID NO 2
<211> LENGTH: 18
<212> TYPE: DNA
<213> ORGANISM: Unknown Organism
<220> FEATURE:
<223> OTHER INFORMATION: Description of Unknown Organism: Bacterial

<400> SEQUENCE: 2
actcctacgg gaggcagc                                                  18

<210> SEQ ID NO 3
<211> LENGTH: 20
<212> TYPE: DNA
<213> ORGANISM: Unknown Organism
<220> FEATURE:
<223> OTHER INFORMATION: Description of Unknown Organism: Bacterial

<400> SEQUENCE: 3
ctcctacggg aggcagcagt                                                20

<210> SEQ ID NO 4
<211> LENGTH: 18
<212> TYPE: DNA
<213> ORGANISM: Unknown Organism
<220> FEATURE:
<223> OTHER INFORMATION: Description of Unknown Organism: Bacterial

<400> SEQUENCE: 4
gctgcctccc gtaggagt                                                  18

-continued

```
<210> SEQ ID NO 5
<211> LENGTH: 20
<212> TYPE: DNA
<213> ORGANISM: Unknown Organism
<220> FEATURE:
<223> OTHER INFORMATION: Description of Unknown Organism: Bacterial

<400> SEQUENCE: 5
actgctgcct cccgtaggag                                               20

<210> SEQ ID NO 6
<211> LENGTH: 18
<212> TYPE: DNA
<213> ORGANISM: Unknown Organism
<220> FEATURE:
<223> OTHER INFORMATION: Description of Unknown Organism: Bacterial

<400> SEQUENCE: 6
tgccagcagc cgcggtaa                                                 18

<210> SEQ ID NO 7
<211> LENGTH: 18
<212> TYPE: DNA
<213> ORGANISM: Unknown Organism
<220> FEATURE:
<223> OTHER INFORMATION: Description of Unknown Organism: Bacterial

<400> SEQUENCE: 7
taccgcggct gctggcac                                                 18

<210> SEQ ID NO 8
<211> LENGTH: 21
<212> TYPE: DNA
<213> ORGANISM: Unknown Organism
<220> FEATURE:
<223> OTHER INFORMATION: Description of Unknown Organism: Bacterial

<400> SEQUENCE: 8
cctgcgtgcg ctttacgccc a                                             21

<210> SEQ ID NO 9
<211> LENGTH: 24
<212> TYPE: DNA
<213> ORGANISM: Unknown Organism
<220> FEATURE:
<223> OTHER INFORMATION: Description of Unknown Organism: Bacterial

<400> SEQUENCE: 9
agcaaacagg attagatacc ctgg                                          24

<210> SEQ ID NO 10
<211> LENGTH: 24
<212> TYPE: DNA
<213> ORGANISM: Unknown Organism
<220> FEATURE:
<223> OTHER INFORMATION: Description of Unknown Organism: Bacterial

<400> SEQUENCE: 10
caggattaga taccctggta gtcc                                          24

<210> SEQ ID NO 11
<211> LENGTH: 22
<212> TYPE: DNA
<213> ORGANISM: Unknown Organism
<220> FEATURE:
<223> OTHER INFORMATION: Description of Unknown Organism: Bacterial
```

<400> SEQUENCE: 11
ggcgtggact accagggtat ct                                          22

<210> SEQ ID NO 12
<211> LENGTH: 18
<212> TYPE: DNA
<213> ORGANISM: Unknown Organism
<220> FEATURE:
<223> OTHER INFORMATION: Description of Unknown Organism: Bacterial

<400> SEQUENCE: 12
ggttaagtcc cgcaacga                                               18

<210> SEQ ID NO 13
<211> LENGTH: 18
<212> TYPE: DNA
<213> ORGANISM: Unknown Organism
<220> FEATURE:
<223> OTHER INFORMATION: Description of Unknown Organism: Bacterial

<400> SEQUENCE: 13
tcgttgcggg acttaacc                                               18

<210> SEQ ID NO 14
<211> LENGTH: 20
<212> TYPE: DNA
<213> ORGANISM: Unknown Organism
<220> FEATURE:
<223> OTHER INFORMATION: Description of Unknown Organism: Bacterial

<400> SEQUENCE: 14
gaggaaggcg gggatgacgt                                             20

<210> SEQ ID NO 15
<211> LENGTH: 20
<212> TYPE: DNA
<213> ORGANISM: Unknown Organism
<220> FEATURE:
<223> OTHER INFORMATION: Description of Unknown Organism: Bacterial

<400> SEQUENCE: 15
acgtcatccc cgccttcctc                                             20

<210> SEQ ID NO 16
<211> LENGTH: 20
<212> TYPE: DNA
<213> ORGANISM: Unknown Organism
<220> FEATURE:
<223> OTHER INFORMATION: Description of Unknown Organism: Bacterial

<400> SEQUENCE: 16
aaggaggtga tccaaccgca                                             20

<210> SEQ ID NO 17
<211> LENGTH: 20
<212> TYPE: DNA
<213> ORGANISM: Unknown Organism
<220> FEATURE:
<223> OTHER INFORMATION: Description of Unknown Organism: Bacterial

<400> SEQUENCE: 17
aaggaggtga tccagccgca                                             20

RIBOSOMAL RNA GENE POLYMORPHISM BASED MICROORGANISM IDENTIFICATION

This application claims benefit of Provisional application Ser. No. 60/045,603, filed May 5, 1997.

FIELD OF THE INVENTION

The invention is the field of microbial taxonomy, more particularly in the field of computer based classification of microorganisms polynucleotide sequences.

BACKGROUND

Currently used methods of microbial identification have numerous shortcomings. Such shortcomings include the need for special growth media, the inability to distinguish closely related species and strains, the need for large amounts of sample, the need to culture the organism for a lengthy period of time, and the like.

The sequence of 16S ribosomal RNA has long been use for analyzing the evolutionary relationship between microorganisms. Many groups have used differentially hybridizing DNA probes (or batteries at such differential probes) in order to identify unknown microorganisms on the basis of hybridization to ribosomal RNA. However, nucleic acid hybridization is an imprecise technique and is ill-suited for distinguishing between closely related strains or species.

The DNA sequences of 16S RNA genes in public databases such as GENBANK have serious problems with regards to accuracy and completeness. These problems arise because many bacteria have two or more 16S ribosomal RNA genes and sequence variations occur between the different copies of the gene present in the same genome, i.e., polymorphisms. Traditional analysis of 16S ribosomal RNA is involves the cloning and sequencing of individual 16S ribosomal RNA genes. In many instances, no publicly available information exists as to the sequences of all of the 16S ribosomal RNA genes in given organism. A similar lack of information exists with respect to other ribosomal RNA genes in bacteria and other microorganisms.

In view of the shortcoming of the commonly used microbial identification systems, it is of interest to provide new gene sequence by sex methods for the identification and classification of unknown microorganisms.

SUMMARY OF THE INVENTION

The invention relates the discovery that the polymorphisms in 16S rRNA genes (and other microbial rRNA genes) may be used to identify unknown bacterial isolates at the level of species, subspecies and strain identification. The invention also relates to the discovery that the sequences of individual ribosomal RNA genes is not required in order to provide identification of an unknown organism. The invention involves the generation of a composite polynucleotide sequence of the 16S rRNA genes (or other microbial rRNA genes) of an "unknown" microorganism of interest. Composite polynucleotide sequences are polynucleotide sequences that are simultaneously derived from the several corresponding polynucleotide sequences, i.e., multiple copies of the same gene, present in the same genome. The use of composite sequences for identification is convenient and efficient because there is no need to isolate one of more individual 16S rRNA genes (or other microbial rRNA genes) from an organism in order to generate a composite polynucleotide sequence. The 16S ribosomal RNA region composite sequences used for analysis purposes may be obtained from the entire 16S ribosomal RNA gene or a portion of the 16S ribosomal RNA gene, i.e., a 16S rRNA region. Composite ribosomal RNA gene sequences in addition to the 16S ribosomal RNA may be substituted for 16S ribosomal RNA genes in the invention described herein.

Another aspect of the invention is to provide methods for identifying microorganisms. The subject methods comprise the steps of generating a composite 16S rRNA (or other ribosomal RNA) region sequence from a microorganism of interest. The composite 16S rRNA region sequence reveals polymorphisms within the 16 ribosomal RNA gene of the microorganism. The composite 16S rRNA region sequence may then be compared with a list of previously obtained composite 16S rRNA region sequences from reference microorganisms so as to determine the species, subspecies, or strain of the microorganism of interest. Preferably, the database is provided in a computer-readable form.

Another aspect of the invention is to provide computer based methods of identifying a microorganism. The computer based methods of the invention involve generating a composite 16S ribosomal RNA (or other ribosomal RNA) region sequence from a microorganism of interest. After the composite 16S ribosomal RNA (or other ribosomal RNA) region sequence has been obtained, the sequence information is entered into an experimental data register of a programmable computer. After entry into the experimental data register, the composite sequence information in the experimental data register is compared against a plurality of data registers encoding a unique composite 16S ribosomal, RNA (or other ribosomal RNA) region sequence that are correlated with a unique microorganism identifying names. The comparison is performed through the use of a sequence alignment comparison algorithm. The algorithm is used to determine the reference data register that best matches the experimental data register as well as determining a list of other closely matching composite sequences.

Another aspect of the invention is to provide polynucleotide primers for the amplification of 16S ribosomal RNA regions and the generation of composite 16S rRNA sequences. The invention also provides kits for obtaining composite 16S ribosomal RNA region sequences. The composite polynucleotide sequences generation kits of the invention comprise primers for the amplification 16S ribosomal RNA genes (or portions thereof). The subject kits may also comprise sequencing primers for obtaining the composite sequences of 16S rRNA gene regions. The kits may also comprise a database of composite 16S rRNA region sequences.

Another aspect of the invention is to provide a database listing of composite polynucleotide sequences of ribosomal 16S RNA in a computer readable form. Ideally, the database is as large as possible and comprises composite 16S ribosomal RNA sequences from most known bacterial species type strains, subspecies, and strains.

BRIEF DESCRIPTION OF THE DRAWINGS

FIG. 1 is schematic representation of the orientation of a set of sequencing primers with respect to a 16S rRNA gene.

DEFINITIONS

The terms "16S ribosomal RNA gene" or "16S rRNA gene" as used herein include not only the 16S ribosomal RNA encoding sequence, but also the 16S ribosomal intergenic region located between the 16 s RNA and the 23S ribosomal RNA gene.

The terms "16S ribosomal RNA region" or "16S rRNA region" as used herein refer to a contiguous polynucleotide sequence that comprises at least 100 nucleotides from the 16S ribosomal RNA gene. 16S rRNA regions may comprise a polynucleotide sequences from (a) the 16S ribosomal RNA encoding sequence, (b) the 16S–23S ribosomal RNA intergenic region, and (c) the 16S ribosomal RNA encoding sequence and the 16S–23S ribosomal RNA intergenic region. The terms "16S ribosomal RNA region" or "16S rRNA region" also include polynucleotides that comprise the entire 16S rRNA gene.

The term "16S ribosomal RNA encoding sequence" refers to the portion of a 16S ribosomal RNA gene that actually encodes the 16S ribosomal RNA from the relevant organism.

The term "composite polynucleotide sequence" refers to polynucleotide sequence information that is generated by combining at least two constituent polynucleotide sequences into a single polynucleotide sequence representative of the constituent polynucleotides so as to indicate the nucleotides bases that are in common between the constituent sequences and the nucleotide bases that vary, i.e., are polymorphic, between the constituent sequences. Composite polynucleotide sequences of the invention may be generated by simultaneously generating sequence information from multiple alleles of corresponding sequences present in the same preparation. The range of different bases that may be present at a polymorphic site is reflected in the composite sequence, e.g., by an IUPAC code variation in which the multiple bases at a position are listed as being simultaneously present (rather than present in the alternative). For example, a composite sequence of sequence (i) "AAATCGTTAA", sequence (ii) "AATTCGCTAA", and sequence (iii) "AAGTCGCTAT" is AADTCGYTAW (IUPAC code, wherein D=A, T and G, Y=T and C, and W=A and T.) It will be appreciated by those skilled in the art that many different coding systems may be used to represent composite sequence information.

The term "microorganism identifying name" refers to the name used to identify a given microorganism isolate and include not only the genus and species name, but may also includes applicable subspecies or strain names (assuming subspecies or strains names have been provided for the associated species).

The term "identifying" refers to the process of correlating a microorganism identifying name with a specific microorganism isolate.

The term "species", unless indicated otherwise by context, includes both the subspecies designation and the strain designation (if applicable).

The term "sequence comparison algorithm" as used herein refers to an algorithm for comparing the similarity of polynucleotide sequences to one another.

The terms "polymorphic site" as used herein refer to location in polynucleotide sequence that varies between different alleles of the same gene within the same genome.

The term "reference microorganism" refers to a microorganism that has been identified with respect to genus and species, includes those microorganism that have also been identified at a subspecies or strain level.

The term "data register" as used herein refers to computer memory that has been configured to store data. The data stored includes sequence information and reference microorganism information.

The numbering system used herein to refer to specific base positions in the 16S rRNA gene is relative to E. coli 16S ribosomal RNA gene number system for E. coli JO 1859 16S ribosomal RNA gene of operon.

A nucleotide position in one copy of a multicopy gene is said to "correspond" to a nucleotide position in another copy of the same gene if the nucleotides are the same distance from the initial nucleotide position of the gene (adjusting for insertions and deletions).

The term "determining a polymorphism" refers to examining the ratio of two or more fluorescence peaks (or the equivalents thereof) indicative of the same nucleotide location in an electrophoresis separation profile and detecting the presence of at least two nucleotide bases at that location. Polymorphisms may be detected in a fluorescence-based automated sequencing apparatus such as in Applied Biosystems 310 or 377 (Applied Biosystems Division of Perkin-Elmer, Foster City, Calif.). It will be appreciated by those skilled in the art that techniques other fluorescence-based sequencing may be used to detect polymorphisms, e.g. the use of radioactive labels; however, fluorescence-based automated sequencing is preferred.

The term "bacteria" as used herein refers to both eubacteria and archeabacteria.

DETAILED DESCRIPTION OF THE INVENTION

The invention relates to the discovery that composite 16S rRNA region sequences may be used for the identification of microorganisms. 16S rRNA gene region composite sequences reveal polymorphic sites between the different copies of the 16 rRNA gene on a given microbial genome. Surprisingly, composite 16S rRNA gene region composite sequences may be used for identifying microorganisms even though the composite sequences are generated without benefit of the complete knowledge of the constituent sequences used to form the composite sequences. For example, 16S rRNA region composite sequences may be conveniently obtained by using PCR (or other nucleic acid amplification techniques) to simultaneously amplify multiple corresponding 16S rRNA regions in the genome of a microorganism of interest, followed by sequencing the simultaneously amplified polynucleotide fragments, thereby providing a composite 16S rRNA region sequence that reveals the sequence polymorphisms. Similarly, composite 16S rRNA regions may be obtained by cycle sequencing. Thus, for example, a composite sequence showing three polymorphic sites (two possible bases at each site) and formed from three copies of the same gene, does not provide sufficient information to determine the exact polynucleotide sequence of each copy of the three genes used to form the composite sequence. Although the description of the invention provided herein is primarily concerned with the generation and use of composite 16S ribosomal RNA sequences, it will be appreciated by those skilled in the art that the invention may be readily adapted for use with composite ribosomal RNA derived from microbial ribosomal RNA other than 16S ribosomal RNA. For example, yeast and fungi have multiple copies of 18S and 25S ribosomal RNA genes. Thus, it will be understood that the teaching herein regarding 16S ribosomal RNA genes and 16S ribosomal RNA regions may be applied to microorganisms that have ribosomal RNA genes that significantly differ in size from 16S rRNA genes.

The subject methods of identifying microorganisms may be used in a variety of fields including, but not limited to, human medicine, veterinary medicine, agriculture, food science, and industrial microbiology. For example, microorganism identification may be used to determine the identity of a microorganisms found in a patients suffering from an infectious disease. Microorganism identification may also be used to monitor food safety by testing for pathogens. Similarly, plants may be checked to determine if they harbor phytopathogenic bacteria. Microorganism identification is also useful in the field of veterinary science. Microorganisms for analysis by the subject methods may be obtained from many sources. Such sources include, but are not limited to, human patients, animal, flowers, seeds, vegetables, and other food products.

Polynucleotides for analysis by the subject methods are purified from microorganisms of interest in order to provide for generation of composite 16S rRNA region sequences. The degree of purification need only be sufficient to support the subsequent procedures, e.g., PCR amplification and sequencing. Conventional methods of polynucleotide preparation may be used to prepare the sample for analysis such as phenol/chloroform, Chelex® resin, and alkaline heat lysis. In those embodiments of the invention in which the composite 16S RNA region sequences are obtained directly from 16S rRNA rather than the 16S rRNA genes, additional steps should be taken to denature the ribosome and reduce RNAse degradation. Different methods of polynucleotide preparation may be necessary for obtaining polynucleotides from different organisms, for example some cell lysis techniques will work for gram negative bacteria, but not for gram positive bacteria. Microorganisms for analysis may be obtained directly from hosts, e.g., patients, fruits, animals, soil, fabrics, etc., or may be obtained from microorganisms cultured from hosts. Preferably, microorganisms are obtained from purified microorganisms cultured from hosts. In some embodiments of the invention, single cells may be used as a source of DNA for analysis, thereby obviating requirements for purified cultures. The polynucleotides samples may be either DNA, RNA or a combination of both. Preferably, the sample is DNA. Preferably, at least 100 µg of DNA is obtained for analysis; however, considerably smaller amounts of DNA may used in the subject methods. Polynucleotide amplification techniques, such as PCR may be used to compensate when only low levels of genetic material are available for analysis.

Once a suitable polynucleotide sample has been prepared, a composite 16S rRNA region sequence may be generated from the sample. The composite 16S rRNA region sequence generated may correspond to the entire 16S RNA gene, i.e., a composite of all 16S RNA genes in the organism of interest, or may correspond a single region or multiple regions of the 16S RNA genes in the organism of interest. The length of the composite 16S rRNA region sequence generated in the subject methods is at least the minimum sequence length required to identify the unknown microorganism at level of precision desired. The minimum composite sequence length required may vary in accordance with the precise location of the region or regions of the 16S RNA gene selected for composite sequence analysis. In those embodiment of the invention in which the composite 16S rRNA sequence corresponds to less than the entire 16S RNA gene sequence, the region or regions of the 16S rRNA selected for analysis display a high degree of variability between species, isolates or strains of interest. The composite sequence length required for identification in the subject methods is at least 300 contiguous base pairs, preferably at least 400 contiguous base pairs, more preferably at least 500 contiguous base pairs, and yet more preferably at least 1000 contiguous base pairs. In a most preferred embodiment of the invention, a composite sequence corresponding to the entire 16S rRNA gene is generated.

Composite sequences may be generated in a variety of ways. Suitable methods of generating composite sequences involve the simultaneous annealing (for sequencing or amplification) to corresponding sites on multiple 16S rRNA regions within the same genome. In a preferred embodiment of the invention, primers anneal to all of the 16S rRNA genes present in a genome. It will be appreciated by those of ordinary skill in the art that by annealing the same primer to corresponding sites at different 16S rRNA regions, multiple sequencing reaction products will be produced. The sequencing products produced from the different annealing sites will differ from one another by virtue of the sequence polymorphisms between the different 16S rRNA genes in the same genome. Because the amplification reaction produce a mixture of different amplification products corresponding to the different 16S rRNA genes in the genome, simultaneously sequencing the amplification products will produce composite sequence information.

In one embodiment of the invention, one or more 16S rRNA regions in the microorganism of interest are amplified by a nucleic acid amplification technique, such as PCR (polymerase chain reaction), prior to polynucleotide sequencing. Amplification technique serves to simultaneously amplify all copies of the 16S rRNA gene present in the genome of the organism to be identified. Detailed protocols for polynucleotide amplification can be found in, among other places, Dieffenbach and Dveksler, *PCR Primer, A Laboratory Manual*, Coldspring Harbor Press, Coldspring Harbor, N.Y. (1995), McPherson et. al, *PCR A Practical Approach*, Vol 1, IRL Press Oxford, England (1991), McPherson et. al, *PCR A Practical Approach* Vol 2, IRL Press Oxford, England (1995), U.S. Pat. Nos. 4,683,202, 483,195, and 4,965,188. These publications also provide detailed guidance on how to design nucleic acid amplification primers. The amplified polynucleotide sequences may then be sequenced using conventional polynucleotide sequencing methods such as chain termination sequencing. The composite sequence information reveals polymorphic sites in the 16S rRNA region sequence analyzed.

PCR, and related polynucleotide amplification techniques employ pairs of primers that bracket the sequences to be amplified. Preferably, the amplification primers are designed to amplify the entire or substantially the entire 16S rRNA gene. However, regions of the 16S ribosomal gene significantly smaller than the entire 16S rRNA gene may use amplified and used to obtain information sufficient for identifying the microorganism of interest. Primers for use in the subject invention may be used to amplify various 16S rRNA regions including: (a) the entire 16 ribosomal RNA gene, (b) a portion of the 16S ribosomal RNA gene, (c) the 16S–23S ribosomal RNA intergenic region, (d) a portion of the 16S–23S ribosomal RNA intergenic region, (e) a portion of the 16S rRNA gene comprising the 16S rRNA sequence and 16S–23S ribosomal RNA intergenic region sequence, (f) a portion of the 16S rRNA gene comprising the entire 16S rRNA sequence and a portion of the 16S–23S ribosomal RNA intergenic region, and (g) a portion of the 16S rRNA gene comprising a portion of the 16S rRNA sequence and the entire 16S–23S ribosomal RNA intergenic region. The entire 16S rRNA gene may be amplified using either a single set of amplification primers or with multiple sets of amplification primers. The different embodiments of the invention may employ amplification primers that hybridize at many different nucleotide location either within the 16S rRNA gene or proximal to the the 16S rRNA gene. Suitable primer annealing sites include, but are no limited to sites at which polymerization is initiated at positions 28 (forward), 338

(forward), 533 (forward), 800 (forward), 1105 (forward), 1194 (forward), 337 (reverse), 513 (reverse), 788 (reverse), 1086 (reverse), 1173 (reverse), 1519 (reverse). The terms forward and reverse are used to indicate 5'–3' orientation with respect to the 5'–3' orientation of the gene. The indication "forward" indicates that polymerization (i.e., sequence ladder generation) occurs in the same 5'–3' orientation as the ribosomal RNA gene. Primer annealing sites may be located outside of the 16S rRNA genes or within 16S rRNA genes.

Sequence information generating techniques employ sequencing primers to provide sequence information beginning at a specific location on a polynucleotide of interest. The location within a polynucleotide sequence from which sequence information is derived is a function of the sequence of the primer and consequently the site at which priming begins. The amount of sequence information obtained from a given sequencing primer will vary in accordance with the particular techniques used to obtain the sequence information. Typically, the length of the sequence obtained is in the range of about 200 to 600 bases. Given that the entire 16S rRNA gene (including the 16S–23S intergenic region) is about 1543 nucleotides in length (*E. coli*), multiple sequencing primers may be necessary to provide sequence information for the entire 16S rRNA gene or a desired portion thereof Annealing sites for sequencing primers are preferably located in regions of the 16S RNA gene that are highly conserved between species and strains. Additionally, hybridization sites for sequencing primers are preferably located in regions of the 16S RNA gene that do not vary between alleles of the 16S rRNA genes in the same genome.

In other embodiments of the invention, composite 16S rRNA region sequence information may be obtained by applying sequence information generation techniques to 16S rRNA genes without initially performing PCR or related amplification techniques. An example of a method of generating a composite sequence of the 16S rRNA genesis obtained without amplifying the sequence prior to sequencing is cycle sequencing. A description of cycle sequencing can be found, among other places, in Murray V., *Nucl. Acid. Res.*, 17:8889 (1989). Typically, cycle-sequencing is a sequencing ladder generating technique comprising the following steps: (a) the hybridization of a primer oligonucleotide to a template for sequencing so as to form a primed template, (b) extending the primer with a DNA polymerase, (c) ending the extension reaction with a chain terminator (e.g., a dideoxy terminator), (d) denaturing the primed template, (e) repeating steps (a) to (d) for multiple cycles. Increasing the number of cycles may be used to increase the amount of labeled polynucleotide produced, thereby compensating for relatively small amounts of starting material.

Composite sequences contain information about polymorphic sites within the composite sequences. These polymorphic sites may be identified by polynucleotide sequence information generating techniques that appear to reveal multiple different bases at the same sequence position. These techniques include the simultaneous generation of two or more sequence ladders from corresponding priming sites at each copy of the gene (when multiple gene copies are present). Thus when the corresponding positions at different copies of the same gene are filled by the same base, a single peak (or other types of detector output) will be observed. But, multiple peaks at the polymorphic positions because of the presence of two or more different nucleotides at the corresponding sites in the different gene copies. Polynucleotide sequence information may be generated by a variety of methods well known to those skilled in the art. Chain termination sequencing (Sanger-type sequencing) is particularly preferred. The presence and location of polymorphisms in composite sequences may be readily detected by using fluorescence based sequence detection systems such as the ABI 310 or ABI 377 (Perkin-Elmer, Applied Biosystems Division, Foster City, Calif.). The polymorphic sites will be revealed as multiple peaks (distinguishable over background) at the same sequence site. Additionally, sequence polymorphisms may readily be detected by non-fluorescence based sequence detection systems such as through the use of radioactive labels.

After the composite sequence of a 16S rRNA region from the genome of an organism of interest has been obtained, the composite sequence may be compared with a database of composite 16S rRNA region sequences that have been obtained from reference microorganisms in order to provide for identification of the unknown microorganism. These sequence comparisons may be conveniently effected by a programmable computer that has been programmed to make polynucleotide sequence comparisons. In other embodiments of the invention, sequence comparisons may be effected without the aid of a computer. In order to make use of a computer to compare composite polynucleotide sequences, the composite 16S rRNA sequence information is entered into a form of information that may be manipulated by a computer, i.e., the composite sequence information is entered into a data register. This data register is referred to herein as an "experimental data register." The sequence information in the experimental data register is subsequently compared with corresponding composite 16S rRNA region sequence information in a reference database in order to determine the identity of the unknown microorganism. The reference databases of the invention comprise a plurality of data registers. Each data register comprises the composite 16S rRNA gene sequence of a reference microorganism or a composite 16S rRNA gene sequence region of a reference microorganism or mathematical representation of the sequence, e.g., a BLAST precompute. In a preferred embodiment of the invention, each reference data register comprises a composite sequence (or the equivalent thereof) of the entire 16S rRNA gene from a reference microorganism. It will be appreciated by those skilled in the art that a plurality of data registers corresponding to the constituent sequences of a composite sequence may be substituted for a single register comprising a composite sequence. The sequence information in each reference data register is correlated with the name of the reference microorganism source from which the sequence data was derived. The correlation between the sequence information in a data register and a microorganism identifying name is such that by selecting a reference data register on the basis of the sequence information in the reference data register, a unique correlated identifying microorganism name is given. The name of the reference microorganism is stored in a data register that may or may not be part of the reference data register.

The invention also provides databases in computer readable form. The database may be used in the subject methods and systems. The databases for use in the invention comprise a plurality of reference data registers, each data register representing a distinct microorganism 16S rRNA composite region sequence. The database may be in any of a variety of computer readable forms such as electromagnetic storage media, electric storage media, electroptical storage media, optical media and the like. Examples of storage media for holding data in computer readable form include storage media such as RAM and ROM, floppy discs, CD-ROM, hard disk storage media, magnetic tape, and the like. The composite sequence information is in the form of a reference data register recording a composite polynucleotide sequence. A variety of data storage structures are known to persons skilled in the art of computer science and may be readily adapted for use in the subject invention. In a preferred embodiment of the invention, the database comprises reference data registers of composite sequence information represent entire 16S rRNA genes. Generally, the more data registers in a database, the more useful the database is because a wider variety of microorganisms may be identified. Ideally, a database would comprise the 16S rRNA genes of all known species, subspecies, and strains of bacteria. Other embodiments of the subject databases include databases that comprise reference data registers of composite sequence information corresponding to the 16S rRNA genes of less than all known species of eubacteria. Databases that contain reference data registers that correspond to less than all known species of bacteria preferably comprise reference data registers corresponding to a substantial portion of known members of a given family or other grouping of physiologically similar bacteria. Such families or groups include, the enterobacteria, gram negative bacteria, gram positive bacteria, anaerobic bacteria, spore-forming bacteria, streptococci, mycoplasma, mycobacteria, and the like. Preferably, the databases of the invention comprise at least data registers for at least 500 different bacteria, and more preferably at least 1000 different bacteria.

Methods of the invention may include the step of comparing the composite sequence information in an experimental data register with the composite sequence information in one or more data registers. The comparison results in the determination of which database register in the database contains composite sequence information that best matches the composite sequence of the experimental data register. Preferably, the best matching composite sequence is a composite sequence that perfectly matches the composite sequence information in the experimental data register. Sequence comparison take into account polymorphic positions in the composites sequences of the experimental data register sequence and the reference data registers. In a preferred embodiment of the invention, the sequence comparisons between the composite sequence information are effected through at least one sequence comparison algorithm executed by a programmable computer. Many algorithms for sequence comparison have been described and may be used to effect the sequence comparisons of the subject methods. Generally, such algorithms involve an identity scoring of a comparison matrix between the composite sequence of the unknown microorganism and a reference data register. Examples of such algorithm include the Needleman-Wunsch algorithm (Needleman and Wunsch, *J. Mol Biol* 48:443–453 (1970), total alignment (Collins and Coulson, Nucleic Acid and Protein Sequence Analysis: A practical Approach" (eds. M J Bishop and C J Rawlings), pp. 323–358. IRL Press (1987), Smith-Waterman algorithm (Collins and Coulson, Significance of protein sequence similarities, Methods Enzymol. 183, 474–486, Academic Press (1990)). When gaps (or insertions) are found during sequence comparisons, the gaps (or insertions) are treated as miscalled bases for the purposes of comparison. This in preferred embodiments, gaps or insertions will neither increase nor decrease the level of similarity between two ribosomal RNA composite sequences.

The invention also include systems or kits for identifying unknown microorganisms. The subject systems include one or more primers suitable for amplifying and or sequencing 16S rRNA regions so that composite 16S rRNA region sequence may be produced. In a preferred embodiment of the invention, the subject kits comprise all primers necessary to obtain composite sequences for entire 16S rRNA genes. Primers may be supplied for the sequencing of both strands of a 16S ribosomal RNA gene. The sequencing primers in a kit may prime at sites sufficiently close together (e.g. 200–400 bases), so as to provide overlapping sequence information, thereby increasing the accuracy of the composite sequence information generated. The kit may further comprise amplification primers for amplifying complete 16S rRNA genes. Kits may further comprise one or more additional reagents required for polynucleotide amplification or sequencing reactions. Such additional reagents include, but are not limited to DNA polymerase, dNTPs, buffers, ddNTPs, fluorescently labeled ddNTPs, buffers, reaction vessels, DNA extraction reagents, and the like. Kits may comprise reagents in premeasured amounts and preformed mixtures so as to maximize the need for liquid manipulation. Preferably, kits contain detailed instructions on how to carry out one or more methods of the invention.

The invention, having been described above, may be better understood by reference to the following examples. The examples are offered for purposes of illustrating the invention and should not be construed as a limitation on the invention.

EXAMPLE

General Procedure for Composite Sequence Generation from an Unknown Bacterial Isolate DNA from a loopful of bacteria grown in liquid broth was extracted using phenol/chloroform, followed by an ethanol precipitation. The extracted DNA was subjected to 30–35 cycles of PCR with AmpliTaq Gold™ as the polymerase. The amplified PCR fragment included the entire 16S rRNA gene, about 1540 bases. Cycle sequencing with primers 0357R, 0531R, 0810R, 1104R, 1193R, 1540R, 0005F, 0338F, 0776F, 1087F, and 1174F was performed in order to obtain a composite sequence. Sequencing primer orientation is shown in FIG. 1.

| Primer Name | Tm ° C. | Sequence (5'-3') |
|---|---|---|
| 0005F | 70 | TGGAGAGTTTGATCCTGGCTCAG [SEQ IN NO:1] |
| 0337F | 65 | ACTCCTACGGGAGGCAGC [SEQ ID NO:2] |
| 0338F | 69 | CTCCTACGGGAGGCAGCAGT [SEQ ID NO:3] |
| 0354R | 65 | GCTGCCTCCCGTAGGAGT [SEQ ID NO:4] |
| 0357R | 69 | ACTGCTGCCTCCCGTAGGAG [SEQ ID NO:5] |
| 0515F | 74 | TGCCAGCAGCCGCGGTAA [SEQ ID NO:6] |
| 0531R | 74 | TACCGCGGCTGCTGGCAC [SEQ ID NO:7] |
| 0584R | 79 | CCTGCGTGCGCTTTACGCCCA [SEQ ID NO:8] |
| 0776F | 66 | AGCAAACAGGATTAGATACCCTGG [SEQ ID NO:9] |
| 0782F | 64 | CAGGATTAGATACCCTGGTAGTCC [SEQ ID NO:10] |
| 0810R | 68 | GGCGTGGACTACCAGGGTATCT [SEQ ID NO:11] |
| 1087F | 64 | GGTTAAGTCCCGCAACGA |

-continued

| Primer Name | Tm ° C. | Sequence (5'-3') |
|---|---|---|
| 1104R | 64 | [SEQ ID NO:12]<br>TCGTTGCGGGACTTAACC |
| 1174F | 72 | [SEQ ID NO:13]<br>GAGGAAGGCGGGGATGACGT |
| 1193R | 68 | [SEQ ID NO:14]<br>ACGTCATCCCCGCCTTCCTC |
| 1540Rn | 72 | [SEQ ID NO:15]<br>AAGGAGGTGATCCAACCGCA |
| 1540Ra | 72 | [SEQ ID NO:16]<br>AAGGAGGTGATCCAGCCGCA<br>[SEQ ID NO:17] |

The primer name is indicative if the position within the 16S rRNA operon the extreme 5' end of the primer anneals to. The terms forward and reverse are used to indicate 5'–3' orientation with respect to the 5'–3' orientation of the gene. F is used to indicate a forward primer. R is used to indicate a reverse primer. The designation "forward" indicates that polymerization (i.e., sequence ladder generation) occurs in the same 5'–3' orientation as the ribosomal RNA gene.

All publications and patent applications mentioned in this specification are indicative of the skill of those skilled in the art to which this invention pertains. All publications and patent applications are herein incorporated by reference to the same extent as if each individual publication or patent application was specifically and individually indicated to be incorporated by reference.

EQUIVALENTS

The foregoing written specification is considered to be sufficient to enable one skilled in the art to practice the invention. Indeed, various modifications of the above-described modes for carrying out the invention that are obvious to those skilled in the field of molecular biology or related fields are intended to be within the scope of the following claims.

What is claimed is:

1. A method for identifying a microorganism, said method comprising; generating a composite sequence of a ribosomal RNA (rRNA) gene region of an unknown microorganism, wherein the composite sequence is generated by simultaneously obtaining nucleotide base sequence data from every copy of the rRNA gene region in the genome of the unknown microorganism, comparing the composite sequence with a plurality of comparable rRNA region sequences in a database comprising composite sequences of comparable rRNA regions derived from a plurality of distinct microorganisms, and identifying an rRNA gene region in the database that matches the composite sequence, whereby the identity of the microorganism determined.

2. A method according to claim 1, wherein the rRNA gene region is at least 100 bases in length.

3. A method according to claim 2, wherein the ribosomal RNA region is selected from the group consisting of (a) the 16S ribosomal RNA gene, (b) a portion of the 16S ribosomal RNA gene, (c) the 16S–23S ribosomal RNA intergenic region, (d) a portion of the 16S–23S ribosomal RNA intergenic region, (e) the 16S ribosomal RNA gene and the 16S–23S ribosomal RNA intergenic region, and (f) a portion comprising the 16S ribosomal RNA gene and the 16S–23S ribosomal RNA intergenic region.

4. A method according to claim 1, wherein the database is in a computer accessible format.

5. A method according to claim 1, wherein the composite sequence of the unknown organism is generated by simultaneously sequencing an rRNA gene region of the unknown microorganism.

6. A method according to claim 5, wherein the sequence generation is by cycle sequencing.

7. A method according to claim 5, wherein the rRNA gene region from which the composite sequence is generated is amplified prior to sequence generation.

8. A method of identifying the species of a microorganism comprising, generating a composite ribosomal RNA (rRNA) region sequence from an unknown microorganism, wherein the composite sequence is generated by simultaneously obtaining nucleotide base sequence data from every copy of the rRNA gene region in the genome of the unknown microorganism, entering said composite rRNA region sequence into a first data register of a programmable computer, comparing the first data register and a plurality of reference data registers, each of said data registers encoding a unique composite rRNA sequence corresponding to the rRNA region composite sequence, wherein each of said reference data registers is correlated with a unique microorganism species name, and wherein the reference data register that best matches the first data register is determined, and displaying the unique microorganism name correlated with the best matching first data register.

9. A method according to claim 8, wherein the composite rRNA region is at least 100 bases in length.

10. A method according to claim 8, wherein the ribosomal RNA region is selected from the group consisting of the 16S ribosomal RNA gene, (b) a portion of the 16S ribosomal RNA gene, (c) the 16S–23S ribosomal RNA intergenic region, (d) a portion of the 16S–23S ribosomal RNA intergenic region, (e) the 16S ribosomal RNA gene and the 16S–23S ribosomal RNA intergenic region, and (f) a portion comprising the 16S ribosomal RNA gene and the 16S–23S ribosomal RNA intergenic region.

11. A method according to claim 8 wherein the reference data register comprises the DNA ribosomal gene sequence information from a microorganisms belonging to a class selected from the group consisting of enterobacteria, gram negative bacteria, and gram positive bacteria.

12. A method according to claim 8, wherein the composite sequence is generated by simultaneously sequencing the rRNA gene regions of the unknown microorganism.

13. A method according to claim 8, wherein the sequence generation is by cycle sequencing.

14. A method according to claim 8, wherein the rRNA gene region from which the composite sequence is generated is amplified prior to sequence generation.

* * * * *